(12) United States Patent
Nedelcu et al.

(10) Patent No.: US 11,666,414 B2
(45) Date of Patent: Jun. 6, 2023

(54) METHODS AND SYSTEMS FOR TRACKING AN ASSET IN A MEDICAL ENVIRONMENT AND DETERMINING ITS STATUS

(71) Applicant: Intelligent Locations, Inc., Deer Park, IL (US)

(72) Inventors: Bogdan R. Nedelcu, North Barrington, IL (US); Ramy S. Ayoub, Arlington Heighls, IL (US)

(73) Assignee: Intelligent Locations, Inc., Deer Park, IL (US)

( * ) Notice: Subject to any disclaimer, the term of this patent is extended or adjusted under 35 U.S.C. 154(b) by 86 days.

(21) Appl. No.: 17/236,840

(22) Filed: Apr. 21, 2021

(65) Prior Publication Data
US 2021/0361382 A1   Nov. 25, 2021

Related U.S. Application Data

(63) Continuation of application No. 16/094,875, filed as application No. PCT/US2017/028385 on Apr. 19, 2017, now Pat. No. 11,007,033.
(Continued)

(51) Int. Cl.
*G16H 20/13*    (2018.01)
*A61B 90/90*    (2016.01)
(Continued)

(52) U.S. Cl.
CPC .............. *A61B 90/90* (2016.02); *A61B 34/20* (2016.02); *A61B 90/98* (2016.02); *G01S 5/01* (2020.05);
(Continued)

(58) Field of Classification Search
CPC ........ G16H 40/20; G16H 20/13; G16H 10/60; G16H 40/67; G16H 10/20; G16H 15/00;
(Continued)

(56) References Cited

U.S. PATENT DOCUMENTS

| 5,900,801 A | 5/1999 | Heagle et al. |
| 7,518,502 B2 | 4/2009 | Austin et al. |

(Continued)

FOREIGN PATENT DOCUMENTS

| WO | 2015/061718 A1 | 4/2015 |
| WO | 2017/184747 A1 | 10/2017 |

OTHER PUBLICATIONS

Extended European Search Report issued in European Application No. 17786565 dated Nov. 15, 2019.
(Continued)

*Primary Examiner* — Dionne Pendleton
(74) *Attorney, Agent, or Firm* — Greenberg Traurig, LLP; David J. Dykeman; Jaime Burke

(57) ABSTRACT

Methods and systems are provided for clinicians in a medical environment to remotely assess the status of an asset without physically going to the specific place where the asset is located. By using sensors and special purpose rooms, the methods and systems provide an accurate view of what is going on with the asset. Furthermore, the methods and systems can be extrapolated to a patient's status (knowing if the patient is asleep or awake, or when the patient wakes up post anesthesia—this would imply that the patient wears a tag).

17 Claims, 12 Drawing Sheets

Related U.S. Application Data

(60) Provisional application No. 62/324,872, filed on Apr. 19, 2016.

(51) Int. Cl.

| | | |
|---|---|---|
| *G06Q 50/22* | (2018.01) | |
| *A61B 90/98* | (2016.01) | |
| *G06Q 10/0833* | (2023.01) | |
| *H04W 4/021* | (2018.01) | |
| *G06Q 10/087* | (2023.01) | |
| *G16H 40/20* | (2018.01) | |
| *G01S 5/00* | (2006.01) | |
| *A61B 34/20* | (2016.01) | |
| *G01S 5/02* | (2010.01) | |

(52) U.S. Cl.
CPC ....... *G06Q 10/087* (2013.01); *G06Q 10/0833* (2013.01); *G06Q 50/22* (2013.01); *G16H 20/13* (2018.01); *G16H 40/20* (2018.01); *H04W 4/021* (2013.01); *A61B 2034/2048* (2016.02); *A61B 2034/2074* (2016.02); *G01S 5/02* (2013.01)

(58) Field of Classification Search
CPC ........ G16H 50/20; G16H 50/70; G16H 70/40; G01S 5/0027; G01S 5/01; G01S 5/02; G01S 1/68; G01S 5/0226; G01S 5/08; G01S 5/14; G06Q 10/06; G06Q 10/0833; G06Q 10/087; G06Q 50/22; G06Q 10/08; G06Q 30/0635; A61B 2050/3007; A61B 50/33; A61B 90/90; A61B 90/98; A61B 2034/2048; A61B 2034/2074; A61B 34/20; G08B 13/2462; G08B 13/1418; G08B 13/2417; G16Z 99/00; H04W 4/021; H04W 4/80; H04W 12/12; H04W 12/126; H04W 24/00; H04W 4/02; H04W 4/029; H04W 48/12; H04W 72/085; H04W 72/10; H04W 88/04; H04W 92/02; A61J 2200/30; A61J 2200/72; A61J 7/0418; A61J 1/03; A61J 2200/70; A61J 2205/20; A61J 2205/30; A61J 2205/60; A61J 2205/70; A61J 7/04; A61J 7/0436; A61J 7/0445; A61J 7/0472; A61J 7/0481; A61J 7/049; H04L 63/10; H04L 43/16; H04L 63/0815; H04L 63/0861; H04L 63/1408; B65C 1/021; B65C 2009/0018; B65C 3/10; B65C 9/0015; B65C 9/26; Y02A 90/10; H04B 5/0062; G06K 7/0008; G06K 7/10366; G06F 21/552; G06F 21/554; G06F 21/572; G06F 21/575; G06F 21/71; G06F 21/81; G06F 21/88; G06F 2221/2101; G06F 2221/2103; G06F 2221/2111; G06F 2221/2115; G06F 2221/2141; G06F 2221/2151; G06F 2221/2153

See application file for complete search history.

(56) References Cited

U.S. PATENT DOCUMENTS

| | | | |
|---|---|---|---|
| 7,855,651 B2 | 12/2010 | LeBlond et al. | |
| 7,877,082 B2 | 1/2011 | Eagle et al. | |
| 8,285,564 B2 | 10/2012 | Perkins | |
| 8,294,585 B2 | 10/2012 | Barnhill | |
| 8,564,431 B2 | 10/2013 | Snodgrass | |
| 8,823,502 B2 | 9/2014 | Berkobin et al. | |
| 8,976,028 B2 | 3/2015 | Caporizzo | |
| 8,988,228 B2 | 3/2015 | Iseri et al. | |
| 8,989,053 B1 | 3/2015 | Skaaksrud et al. | |
| 9,060,655 B2 | 6/2015 | Iseri et al. | |
| 9,183,729 B2 | 11/2015 | Hines et al. | |
| 9,785,744 B2 | 10/2017 | Johnson et al. | |
| 10,132,916 B2 | 11/2018 | Nedelcu | |
| 10,229,491 B1* | 3/2019 | Rush | G06T 7/73 |
| 10,401,082 B2 | 9/2019 | Coradetti et al. | |
| 11,007,033 B2 | 5/2021 | Nedelcu et al. | |
| 2005/0250552 A1 | 11/2005 | Eagle et al. | |
| 2005/0253725 A1 | 11/2005 | Neuwirth et al. | |
| 2008/0001735 A1 | 1/2008 | Tran | |
| 2008/0319576 A1 | 12/2008 | Vahlberg et al. | |
| 2009/0109033 A1* | 4/2009 | Salvat | G01S 5/0027 340/572.1 |
| 2009/0167531 A1 | 7/2009 | Ferguson | |
| 2012/0248140 A1 | 10/2012 | Iseri et al. | |
| 2013/0030915 A1 | 1/2013 | Statler et al. | |
| 2013/0122807 A1 | 5/2013 | Tenarvitz et al. | |
| 2013/0250823 A1 | 9/2013 | Gaylard et al. | |
| 2013/0257615 A1 | 10/2013 | Iseri et al. | |
| 2013/0262034 A1 | 10/2013 | Iseri et al. | |
| 2013/0334248 A1 | 12/2013 | Iseri et al. | |
| 2014/0152466 A1 | 6/2014 | Wiesner et al. | |
| 2014/0229196 A1 | 8/2014 | Perkins | |
| 2014/0240125 A1 | 8/2014 | Burch et al. | |
| 2014/0266730 A1 | 9/2014 | Hines et al. | |
| 2014/0339248 A1 | 11/2014 | Reddy et al. | |
| 2015/0002274 A1 | 1/2015 | Sengstaken, Jr. | |
| 2015/0154847 A1 | 6/2015 | Oliver et al. | |
| 2015/0339445 A1* | 11/2015 | Gruby | G16H 40/20 705/2 |
| 2016/0267772 A1 | 9/2016 | Iseri et al. | |
| 2016/0350564 A1 | 12/2016 | Nedelcu | |
| 2017/0061375 A1* | 3/2017 | Laster | G16H 50/30 |
| 2017/0095405 A1* | 4/2017 | Afsarifard | A61J 7/0472 |
| 2018/0154514 A1 | 6/2018 | Angie | |
| 2018/0204111 A1* | 7/2018 | Zadeh | G06N 3/0436 |
| 2019/0053470 A1 | 2/2019 | Singh et al. | |
| 2019/0101616 A1 | 4/2019 | Nedelcu | |
| 2019/0125486 A1 | 5/2019 | Nedelcu et al. | |

OTHER PUBLICATIONS

PCT International Search Report in International Application No. PCT/US2017/028385 dated Oct. 26, 2017.

\* cited by examiner

FIG. 8

METHODS AND SYSTEMS FOR TRACKING AN ASSET IN A MEDICAL ENVIRONMENT AND DETERMINING ITS STATUS

RELATED APPLICATIONS

This application is a continuation patent application of U.S. application Ser. No. 16/094,875, filed Oct. 18, 2018, which is a U.S. national phase application of PCT International Patent Application No. PCT/US2017/028385, filed on Apr. 19, 2017, which claims the benefit of and priority to U.S. Provisional Application Ser. No. 62/324,872, filed on Apr. 19, 2016, the entirety of each of which is hereby incorporated herein by reference in its entirety.

FIELD

The present disclosure uses a new radio technology to not only determine the location of the assets but also to determine their status identified with respect to the needs of the personnel using it in an everyday operation.

BACKGROUND

In the medical field, we designate an asset as any medical instrument which is used during the clinical process. They can be bladder scanners, medication pumps, beds, etc. But in the asset category we can also include desktop computers, laptops, tablets or any object which can change location. The need for tracking assets in a medical or hospital environment is a common, well documented process using RFID technology. It provides the hospital personnel with the ability to know where the needed assets and people are, improving efficiencies and reducing the time required to chase these assets around.

SUMMARY

In any meshed network or similar network with radio coverage within a building or warehouse, where regular GPS reception is not available, this method allows personnel to more efficiently operate and keep track of their assets and patients.

In one aspect, an algorithm provides the location of an asset and determines its state based on inputs automatically generated by the location and sensors attached to it. The sensors are active and can broadcast an identifier and/or payload data such as 3D acceleration coordinates, temperature, heart rate, etc. This data is sent to aggregators that are fixed and located anywhere in the hospital to achieve ubiquitous (or approximately ubiquitous or not ubiquitous) coverage so that they can capture the sensor's signals (and data). The aggregators transmit the data received from sensors and send it to a central computing system where the algorithm resides. The algorithm uses the data to indicate the location and state of the asset or patient.

The more diverse readings we can get from the sensor, the more accurate the algorithm to determine the status can get, but also more complex. In one embodiment, the algorithm is executed with 3 parameters. In one embodiment, these 3 parameters have different weights in the way they are used. They are: location, accelerometer and temperature.

Location: this is an overriding parameter which can, in itself, give the status of an asset, irrespective of the two other parameters. For instance, certain locations have a defined purpose which automatically defines the state of the asset. In the hospital environment, each room has a specific role: for instance, an Operating Room is the place where most surgeries occur, Steril Room is a room where assets are sent to be sterilized before they are re-allocated to the next patient, PACU (Post Anesthesia Care Unit) is the area where patients are placed post surgery, and so forth. In an embodiment, when an asset is placed in a purpose room (e.g. Sterile), the asset will not be available for re-allocation since it needs to be cleaned. So the purpose of the room overrides the status. Accelerometer: can be used in a binary form to give the state of movement of an asset (still/in motion, so a binary representation) or can be used across the 3 spatial dimensions X, Y, Z to further profile the type of movement—a vertical fall for instance will have a sudden change in Z, but very little change in X or Y values.

Temperature: a reading of the temperature.

In some embodiments, a method is provided that includes transmitting parameter data relating to an asset to a central computer, the asset include one or more tags positioned thereon for transmitting the parameter data, and determining a status of the asset based on the parameter data using an algorithm on the central computer. The parameter data comprises accelerometer data relating to movement of the asset through a specified area such that the movement of the asset is used to determine the status of the asset.

The method further includes creating a geo-fence within a space defining the specified area using a plurality of aggregators, with each aggregator capable of communicating with neighboring aggregators and with the central computer over a network. The method includes determining a location of the asset within the area of the geo-fence, and determining the location of the asset relative to the aggregators forming the geo-fence.

In some embodiments, the status of the asset comprises an in use status such that an activity timer associated with the movement of the asset does not exceed a threshold. In some embodiments, the status of the asset comprises an idle status such that an activity timer associated with the movement of the asset exceeds a threshold, indicating that the asset has remained unmoved for a threshold amount of time. In some embodiments, the status of the asset comprises an available status such that the asset is determined to be located within a location indicating that the asset is available for use. In some embodiments, the status of the asset comprises an unavailable status such that the asset is determined to be located in a location indicating that the asset is unavailable for use.

In some embodiments, the status of the asset is used to compile a profile of the asset over time to determine a usage rate of the asset. The profile can determine if an asset is being used. In some embodiments, the asset is in the form a medication dispenser, and the profile determines if a medication stored in the medication dispenser is being taken by a patient at a prescribed dosage rate.

In some embodiments, a method is provided that includes selecting an asset from a list of assets on a mobile application located in a specified area, transmitting the selected asset information from the mobile application to a central computer instructing the central computer to increase the transmission rate of information from one or more tags positioned on the asset, the one or more tags positioned thereon for transmitting a parameter data related to the location of the asset, transmitting a message comprising the increased transmission rate to the tag of the asset, and determining the location of the asset based on the parameter data transmitted from the tag at the increased transmission rate using an algorithm on the central computer. The transmission rate is reset to an initial transmission rate when the asset has been located, the initial transmission rate being lower than the increased transmission rate.

In some embodiments, a method is provided that includes transmitting parameter data relating to an asset to a central computer, the asset include one or more tags positioned thereon for transmitting the parameter data, and determining a status of the asset based on the parameter data using an algorithm on the central computer. The status of the asset is used to compile a profile of the asset over time to determine a usage rate of the asset.

In some embodiments, the profile over time is determined using accelerometer data relating to movement of the asset such that the movement of the asset is used to determine the status of the asset over a specified time period. The profile of the asset over time correlated to the usage of the asset over time. In some embodiments, the one or more tags receive parameter data from a plurality of sensors. In some embodiments, the asset is in the form a medication dispenser, and the profile determines if a medication stored in the medication dispenser is being taken by a patient at a prescribed dosage rate. Movement of the medication dispenser can be detected, including movement associated with opening the medication dispenser. In some embodiments, the profile of the asset over time is formed from a plurality of statuses over time, and wherein increasing the amount of statuses in the time period is effective to increase the accuracy of the profile of the asset.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 8 illustrates an embodiment of a user interface of a mobile application for locating an asset;

DETAILED DESCRIPTION

Figure 1B:
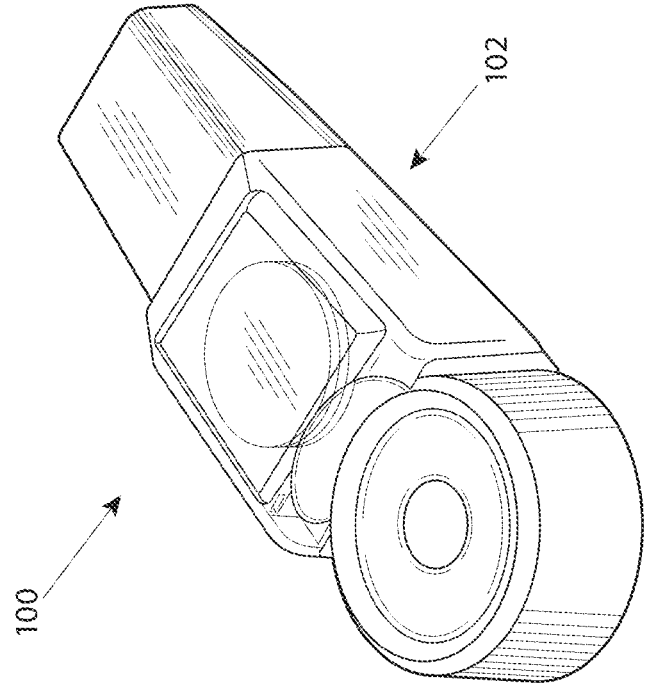
FIGS. 1A and 1B illustrate an embodiment of an asset in the form of a pump handle and a tag for use in locating the pump in a specified area.

The present disclosure provides a method and system for determining the status of an asset which can be mobile, either self-propelled or with the help of an external force. For example, an asset can move independently or can be moved by human intervention (e.g. a bladder scanner can be moved from one room to another room by a nurse to perform a diagnostic). The methods and systems described herein can be produced inexpensively and can have a variety of applications. In some embodiments, the location of the asset can be detected remotely. In some embodiments, the system can determined whether the asset is moving, for how long, etc. In some embodiment, the system can also detect if an asset left the area created by the network formed by the aggregators.

It can be understood that the area (for example, a hospital, a warehouse, etc.) is covered by a network of aggregators placed such that they provide coverage (ubiquitous or not) in the areas of interest of the hospital/warehouse. In some embodiment, the aggregators can be in communication with a computing device, such as a central computer, via a network, such as the Cloud. The central computer has a computing function and a database repository for all data needed to be stored or data which is recorded from various operations, including but not limited to events, measurements, etc.

The systems and methods described herein can be used in a variety of applications where there is a need to remotely monitor the location and status of an asset or person, including but not limited to the medical field. A combination of parameters, such as accelerometer data (moving) and temperature readings, can provide a more precise idea of the status of an asset rather than just one of the two parameters. It will be understood that information regarding more than one parameter increases the precision of information regarding the related asset.

For the medical field, the one or more sensors are attached to the assets. In some embodiments, self-dispensing medication pumps comprise several elements which together perform the desired clinical function which is to dispense pain medication to the patients. For example, the pumps can have 3 different elements which, when assembled together, form the pump. The 3 elements are the "brain", the PCA pump, and the bolus cord. The "brain" is the base of every pump and controls any component attached to the unit. The second component is the PCA pump. It is the pump that delivers the pain medication to the patient. This component is considered a module that will work when connected to the "brain" component. The last component is the PCA pendant (or handle) that is a controller that delivers drugs to the patient; it is a cord that attaches to the PCA pump. The handle is the part that the patient picks up to push the central button on the top of the handle. One or more multi-purpose sensors can be positioned on the handle. When the patient or other user picks up the handle to self-administer the pain medication, the sensor positioned on the handle can detect motion and send the event (for example, binary or 3D coordinates and/or the temperature reading) via Bluetooth or other wireless technologies embedded in a tag. The tag is a small circuit board, powered by a small battery which can send radio signals at regular intervals and with a certain power. The parameters (for example, signal frequency and power levels) are adjustable in software. The signals can be of different radio technologies (Bluetooth, Zigbee, Wi-Fi, Ultra Wide Band, etc.) and contain any type of payload data, or no payload at all. Since they are independently powered, they can be appended to any asset and move with the asset. The fixed aggregators will receive the message sent by the tags, send them to the cloud, or other network, where an algorithm running on the central computer decodes the values and makes a determination as to the action/no action needed to be taken to update the status of the asset (for example, the pump).

Figure 1A:
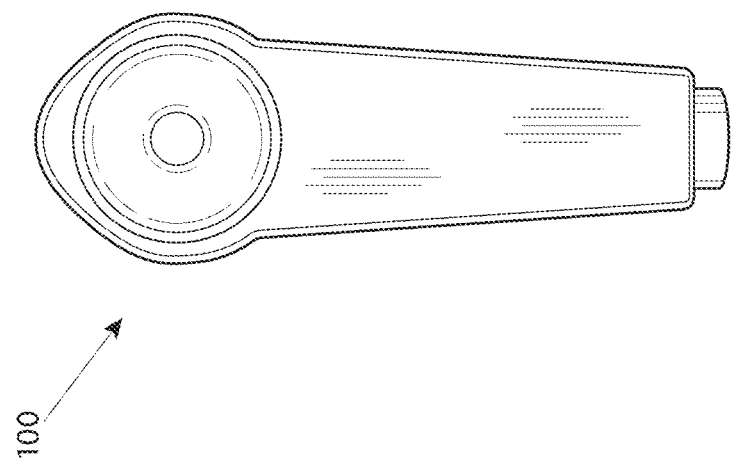

FIGS. 1A and 1B illustrates views of a pump handle 100 and a tag 102 associated with it. The usage patterns of the pump handle depends from patient to patient and is rather broad in the type of motion used to pick up the handle. However, a self-learning algorithm can be implemented to detect the changes in X, Y, Z and model the different spatial patterns through repetition.

Most of the patient's behavior monitored by clinicians—and the advice they give the patients—is to keep the handle near their body so that it becomes easier to find the handle and administer the pain medication. If this is the case, the sensor will record a higher temperature since the patient's body temperature is higher than the ambient temperature in the hospital. That alone can give us an indication that the pump is in use by a patient. The recording of the movement will give us a more accurate view about when the patient used the pump last.

If the temperature is constant and higher than the ambient temperature but there is no movement detected, this can, for example, indicate that the patient is sleeping. If the temperature is equal to the ambient temperature and movement is detected, that means that the patient has the pump handle in a support away from his body and that it just picked the pump to self-administer the pain medication or that a nurse or other hospital personnel moved the pump or the pump handle.

In one embodiment, the same method can be used to detect theft. For example, there can be an asset which is not supposed to leave a certain area, such as the hospital/warehouse. The aggregators installed inside the area, such as the hospital, can create a geo-fence in the same way that a cellular network (Verizon Wireless or AT&T Wireless) provide coverage maps—when you are outside the coverage maps, there is no service on your cell phone. In a similar fashion, the aggregators provide a coverage limited by the distance between the location of the tag and the location of the aggregator. If a tag (or an asset that was tagged) goes beyond the maximum distance after which the aggregator cannot receive the signals transmitted by the tag, then we define this event as "Breaking the geo-fence".

If an asset breaks the geo-fence created by the wireless network formed by the aggregators and the temperature changes suddenly, it is very likely that the asset is outside the hospital/warehouse. The central computer will record the last know aggregator which received the signals from the tag appended to the asset and the time. If the person stealing the device is tagged with a sensor, then the algorithm can associate the readings coming from both the asset and the person and determine (using, e.g., radio correlation techniques) with a high probability the identity of the person stealing the asset.

Figure 2:
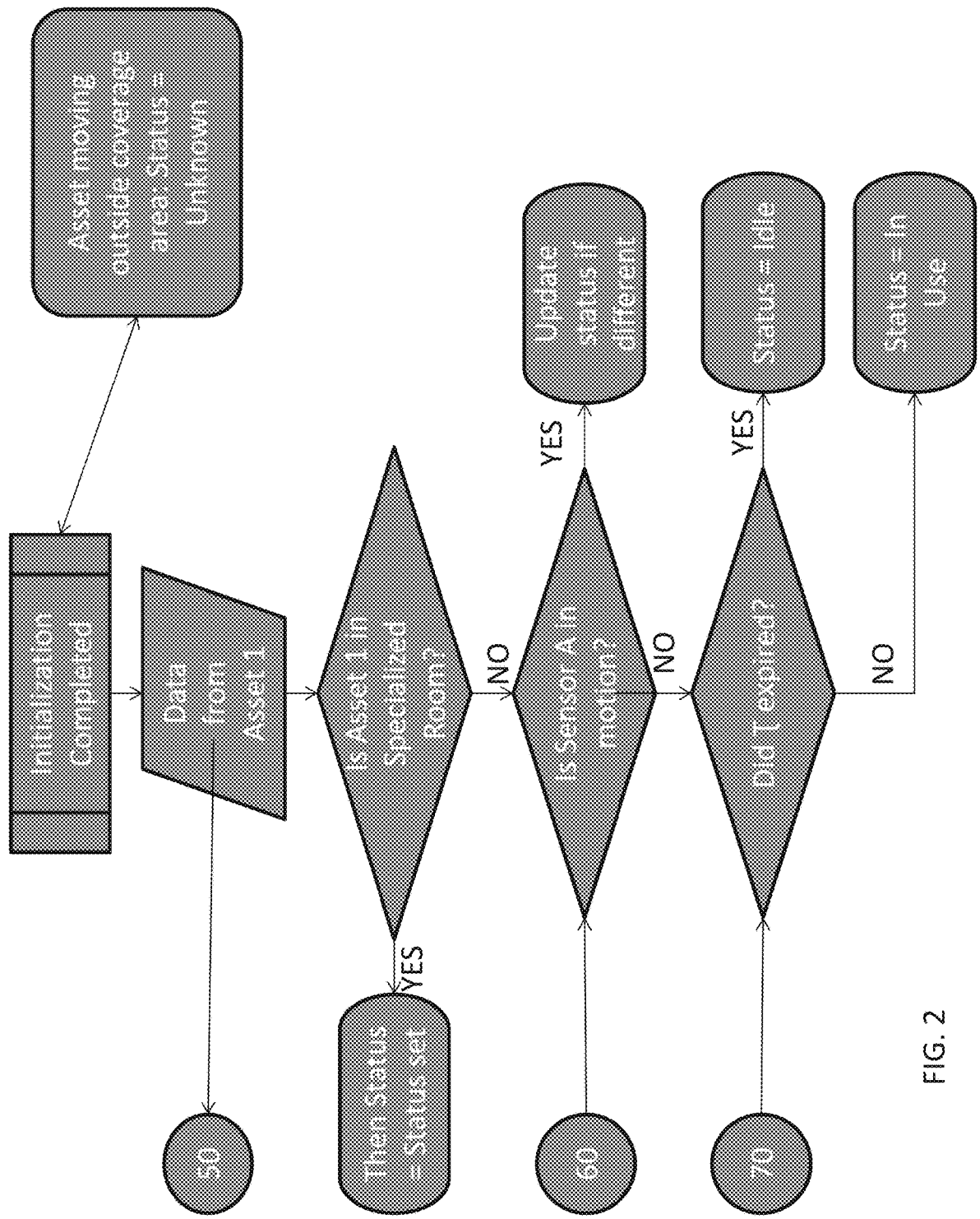
FIG. 2 is a flowchart of an embodiment of an algorithm for determining a status of an asset.

FIG. 2 illustrates an exemplary embodiment of an algorithm implemented in a customer location.

Figure 3:
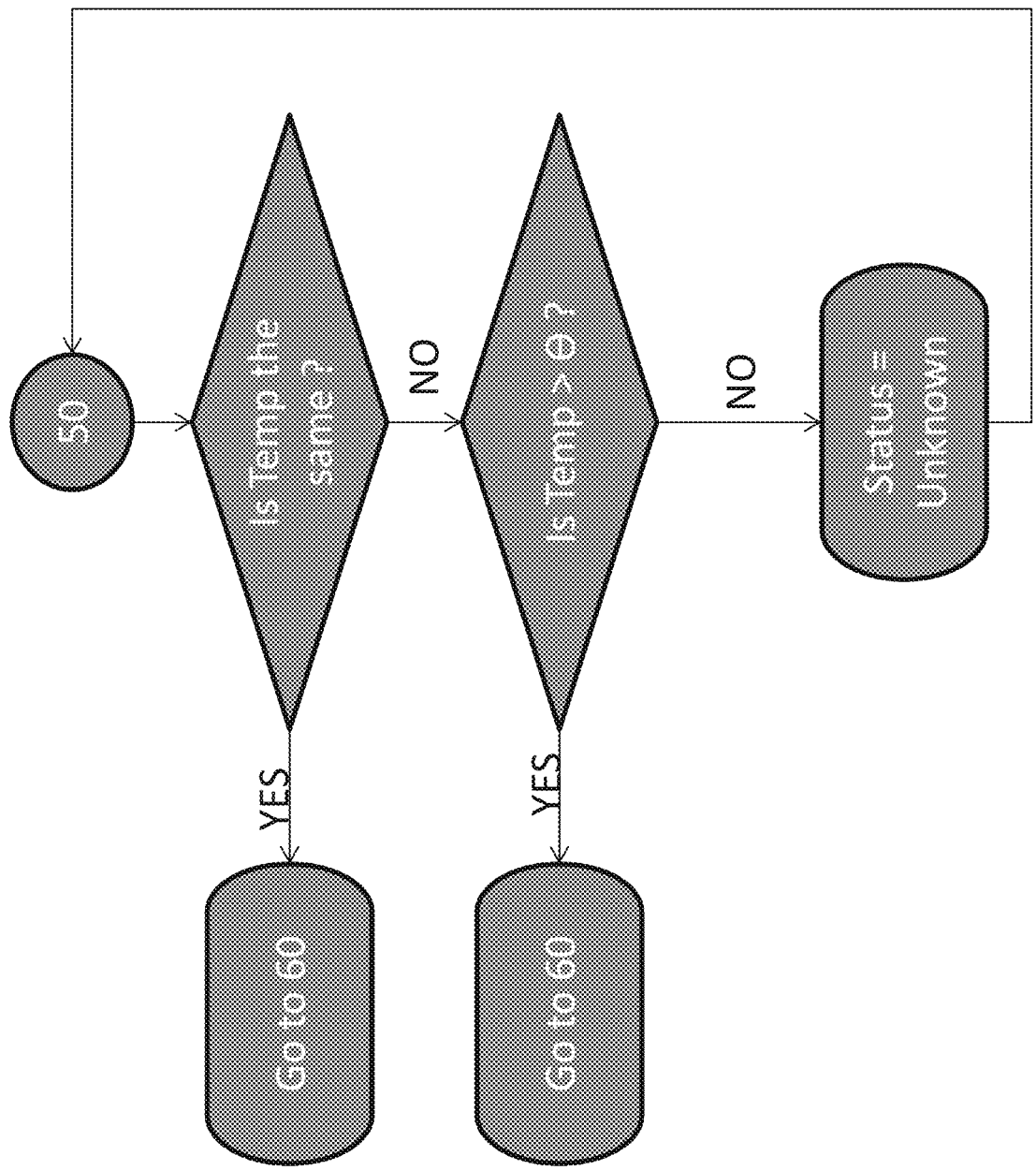
FIG. 3 is a flowchart of an embodiment of an algorithm for determining a status of an asset.

FIG. 3 illustrates another exemplary embodiment of an algorithm in the form of a flow diagram.

There are a variety of states that can define an asset. Examples of different possible states of the asset can include:

a) Status="In Use" when the system receives accelerometer data from a beacon attached to an asset, for example a pump, and an activity timer does not exceed a predetermined time, such as one hour (in one embodiment, this timer is configurable by a superuser). In some embodiments, the superuser is defined as having complete access to the system to perform all tasks possible: add users, remove users, shut down the system, reboot the system, allocate roles and responsibilities for other users, and many more. The superuser is the person in charge of the whole system.

b) Status="Idle" when the activity timer has exceeded the predetermined time, e.g., one hour.

c) Status="Available" when the asset, such as the pump, is in the cage (this is where the pumps (or any asset) go after being sterilized and/or repaired).

d) Status="Unknown" when we have lost the signal with the pump.

e) Status="Unavailable" when the asset, such as the pump, is in a biomed rooms, in sterile, or any detectable area where the asset is not available for usage. The biomed room is the purpose room where the bioengineering department resides. Their role is to manage all assets, including repair, tagging, identifying, inventory, etc.

The followings are exemplary steps for PCA Pump asset type:

1. Asset is registered into the system and gets a beacon: -> status: Unknown;
2. Asset is put to a patient and used:
   a. If movement is detected once (or a predetermined number of times) during the predetermined time period, e.g., one hour (parameter-this means that after each movement we start a timer which is another parameter as it can be changed in the Software), status: In Use;
   b. If no movement detected for the predetermined time period, e.g., one hour, status: Idle;
   c. If the asset registers movement again, after being Idle, it becomes In Use
   d. Asset gets to Biomed, Sterile and along the way -> status in Unavailable; once a gateway from Biomed or Sterile receives signal from the asset, Unavailable status overwrites all other possible statuses.
   e. Asset doesn't send signal to any gateway, status: Unknown;
   f. Asset is seen by the gateway from Cage, status: Available -> set status for specific asset type in area that represents Cage (in UI); In one embodiment, all other possible statuses are overwritten by the area's status for a specific asset type.
   g. Asset gets to PACU, gateway from PACU registers signal from the associated beacon => status: Available
   h. if an area has no status associated to it, status: Unknown;

There are a variety of ways to determine when an asset status becomes "In Use." For example, movement can be registered on all coordinates in any moment.

TABLE 1

| Area | Status for PCA Pump |
|---|---|
| PACU | Available - no movement; |
| Moving to other gateways/areas along the way to the bed - constant moving (>120 s) and losing the signal | Unknown |
| If signal is received and movement is constant >120 s | Unknown |
| Floor -> bed (North/south) - no constant moving (>120 s) and location known | In use/Idle |
| Same logic as from PACU to Floor | Unknown |
| Moving to Biomed/Sterile/Cage | Unavailable |
| Biomed/Soil - ignore the movement | Unavailable |
| Sterile - ignore the movement | Unavailable |
| Cage - ignore the movement | Available |
| Unknown | Unknown |

Generic Algorithm

Specific Room is a room (area) which has a very specific role and uniquely defines the state of the asset Sensor A is a sensor triggered by motion. Sensor A is binary or can send a change in space-time coordinates: X, Y, Z, t Sensor B is a temperature sensor and only provides a reading of the temperature around the tag Initialization:

Possible Statuses are: Unknown, Idle, Available, In Use

Figure 4:
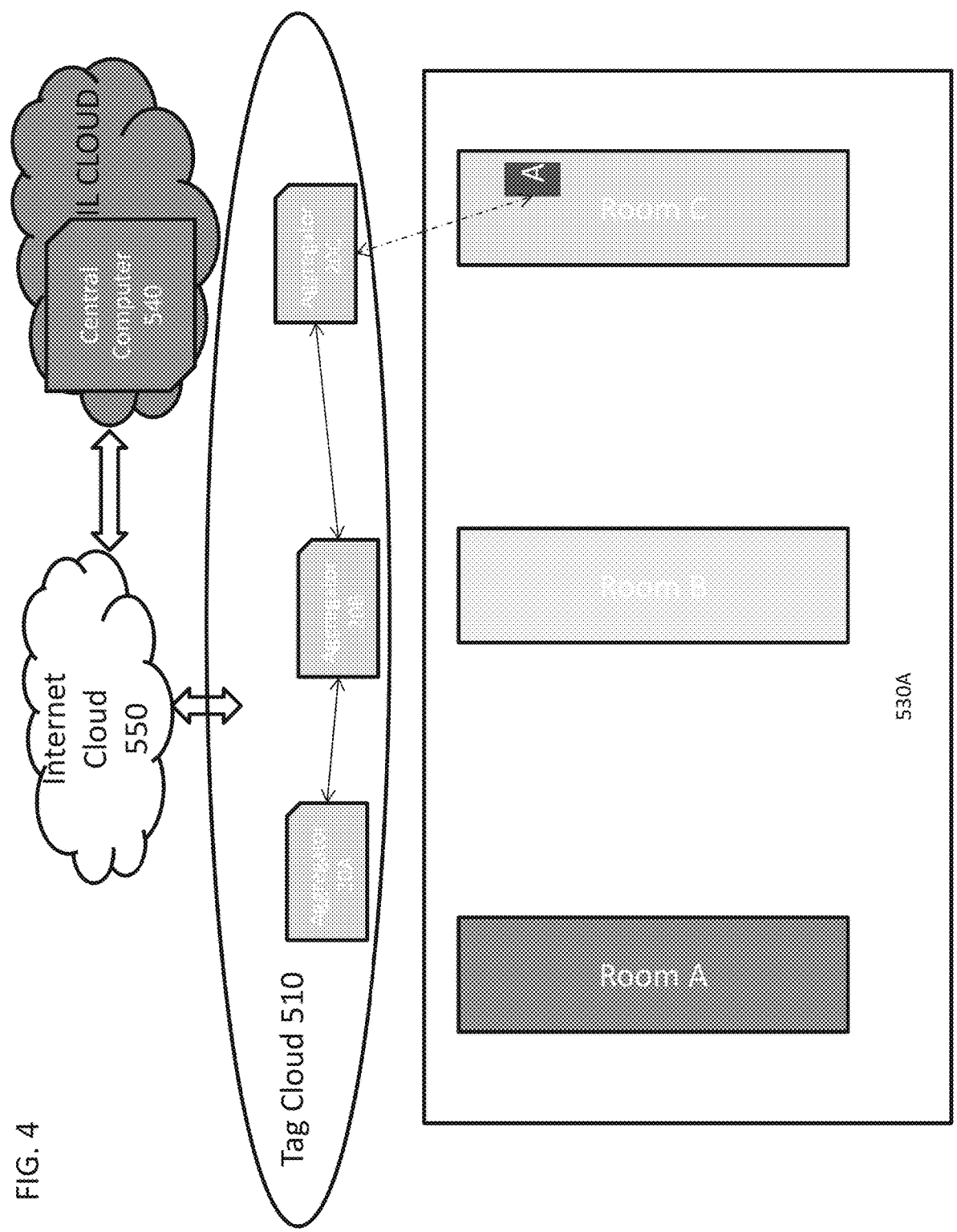
FIG. 4 is an embodiment of a system for determining the location of an asset.

Each Specific Room has a predefined state for the asset; when an asset arrives in a specialized Room, the location overrides the data received from Sensor A or Sensor B Each tag is initialized with the "Unknown" status Temperature in hospital set to θ degrees centigrade Inactivity timer T is preset to 3600 seconds FIG. 4 illustrates the location of an asset "A" determined by an aggregator, for example an aggregator 20C.

In some embodiments, the accelerometer may be placed directly on the dispensing button of the device. The spatial displacement detected by the accelerometer within a specific axis and within a specific range can indicate that the dispensing button has been pushed and the device is in use. In some embodiments, the accelerometer reports the spatial motion to the aggregators, which in turn will forward the data to the status determination algorithms in a backend server (or the central computer). The backend server will compare the spatial movement axis and distance with calibrated parameters. If the comparison yields a determination that the dispensing button has been depressed, the status of the device will be set to "in use".

Figure 5:
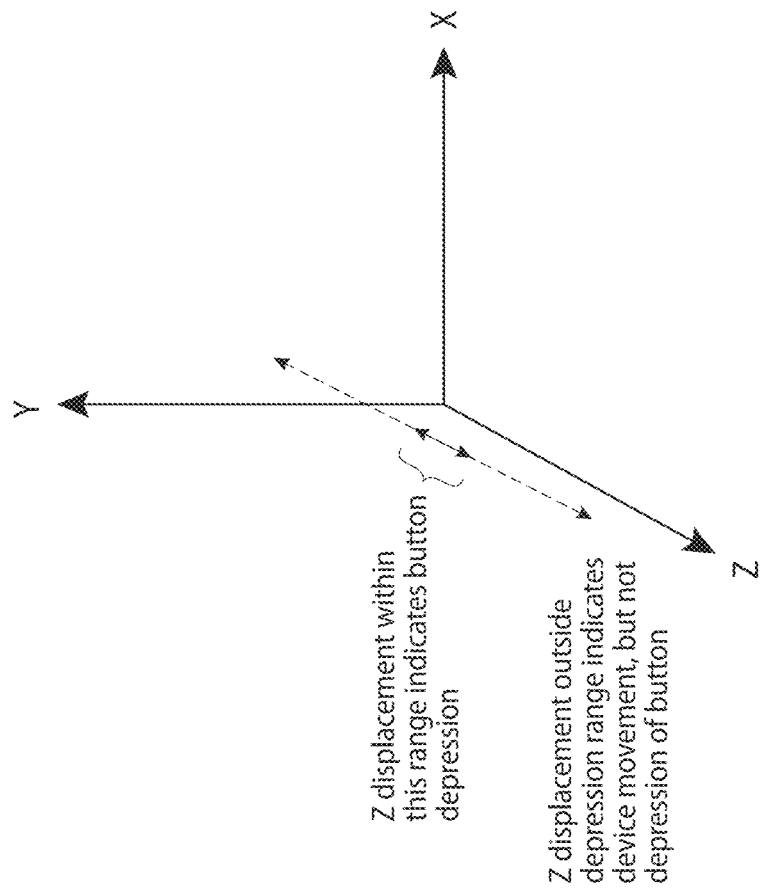
FIG. 5 illustrates an exemplary 3D view of the displacement of an asset.

FIG. 5 illustrates an exemplary 3D view of the displacement of an asset.

To further refine the algorithm, the location of the asset would give greater resolution as to the status of the device. For example, if the accelerometer data, as determined by a server (or central computer), indicates the button is in use and the aggregators locate the signal from the accelerometer to be coming from the biomed purpose room, then the algorithm will combine the accelerometer spatial data with the aggregator data to conclude that the status of the asset is "calibrating", or in use by calibration. If the accelerometer data indicates that the button has not been depressed, but has been moved, and the aggregator data indicates that the asset is in the biomed room, then the status may be set to "Unavailable" (the biomed purpose room is where the assets are repaired, calibrated for further usage). If the accelerometer is reporting spatial movements that are identified as a dispensing button depression, and the aggregators are indicating that the device is in the PACU, then the status can be set to "In use by patient".

The cage is the purpose room where the assets are stored after they have been sanitized. The status of the assets in the cage can be listed as "Available" and override any type of other parameter.

There can be devices that comprise a plurality of components. For example, a device can include two components, one fixed and one attached to, or accessible, to a user. In this case, in some embodiments, one set of motion and/or temperature sensors can be positioned on the fixed portion, and one set of motion and/or temperature sensors can be positioned on the user accessible or fixed portion. When the two motion sensors are logging identical motion parameters from the accelerometer, and the two temperature sensors are reporting identical temperature measurements, then the algorithm will determine that the device, or asset, is not in use, or "available". If the two motion sensors or two temperature sensors are logging different measurements, then the algorithm will determine that the device is in use. If the temperature sensors are logging different temperature readings, with the user affixed or accessible logging higher temperatures, then the algorithm will determine that the device is in use. The closer proximity to humans will be detected as higher temperatures and, therefore, the user accessible section is near a human and in use. Likewise, if the motion sensors on the fixed and moveable portion of the device are logging different readings, then, in one embodiment, it is safe to assume that the device is in use. In this embodiment, the location information gathered by the aggregators will also provide refinement into the type of usage. For example, if maintenance or calibration personnel are working on the device, then the algorithm needs to distinguish between in use by a patient and in use by the maintenance or calibration personnel. The location information will be the deciding factor in the algorithm that will provide the determining factor on the status of the device.

In some embodiments, the algorithm can be enhanced using machine learning patterns around the same parameters to profile each type of asset, or machine, that has a working (in use, idle, off) profile in order to be able to decide when the machine is available for usage, to understand the usage rate for preventive maintenance, and to negotiate better rates for depreciation and trading in of the machine.

Each asset (e.g., machine/pump) has a specific vibration pattern, and current consumption needs that can be profiled using multiple sensors. The idea is to be able to detect with a high level of confidence when a device is in use if they are not equipped with reporting capabilities (as this is the case for most of the currently deployed assets in the hospitals, for instance).

This algorithm can be used in a variety of industries. For example, injection molding companies can use the algorithm to determine, for example, how long an injection molding machine is in use, or how many times the mechanical parts are active. Machine learning and profiling in software can be also used in pharmaceutical applications. For example, a small BLE tag can be placed in the cap of a medication bottle. The profiling can be dissected in small steps (tasks) that are profiled using accelerometers in a lab. Then loaded in the cloud, the different profiles are loaded in a database where they reside and get further enhanced by machine learning techniques.

For example, a patient can store the medication in a closet. The process of taking a medication can be dissected into a number of steps. The patient or user can pick up the bottle from the storage location, for example the closet. Different sized people can produce different types of SW signature as reported by accelerometers placed in the cap of the medication bottle, which can also detect small children patterns and sound alarms if they are not supposed to touch that medication. The medication bottle is moved for a certain amount of time, and the bottle cap or lid is removed, for example, by twisting or pulling up. The cap or lid can be rested on a table or nearby place, and the medication is taken. The cap or lid is returned to the bottle, and the bottle is replaced in the initial storage location, or another location. There is also a temporal dimension that needs to be taken into account when the profile is recorded.

This profiling can be of significant value for drug companies during a clinical testing of new drugs. Knowing with an enhanced level of probability that the patient did indeed take the medication can lead to substantial gains in clinical approval or denial of the drug by the FDA. This can also be used by hospital personnel to monitor patients that were just released in order to check compliance with following the treatment after they have been discharged.

Figure 6:
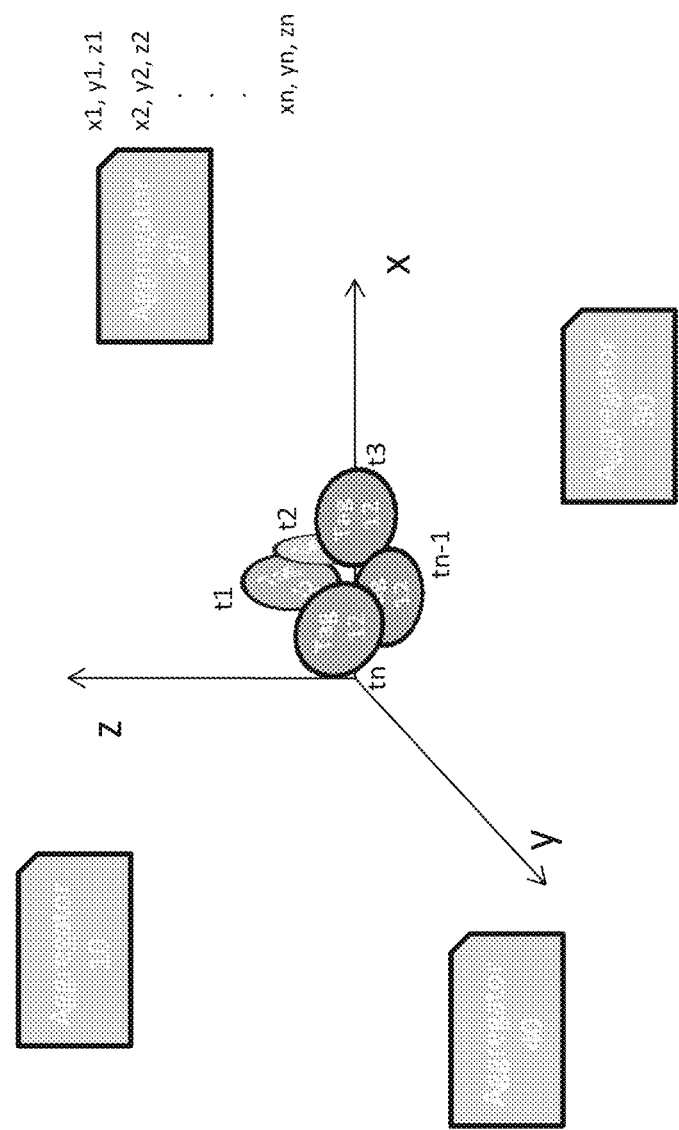
FIG. 6 illustrates an exemplary 3D view of the displacement of an asset.

FIG. 6 illustrates an exemplary profiling method. As shown in FIG. 6, a plurality of aggregators 10, 20, 30, 40 are configured to receive coordinates(x1, y1, z1) to (xn, yn, zn) from Tag12 at instants t1... to tn. The coordinates describe a specific point in time for the movement of Tag12, and are recorded by the central computer at every t increment. The coordinates are stored locally in a database and labeled specifically based on the type of movement was executed.

In some embodiments, in order to increase the likelihood of recognizing an event of interest that occurred when the system is deployed, the same movement must be executed thousands of times to ensure a large database of x,y,z values are available. Each movement type is then categorized and stored in the database of the central computer as a mathematical being which can be used instantly when recognizing events which are happening in real life applications. The higher the segmentation (shorter t interval and smaller the value of n), the higher the likelihood that the correct event is recognized. However, this comes at the expense of large amounts of processing power required to reconstruct in (almost) real time the specific event (hands washing, vibration of a pump, usage of a PCA pump by a patient, etc).

Figure 7:
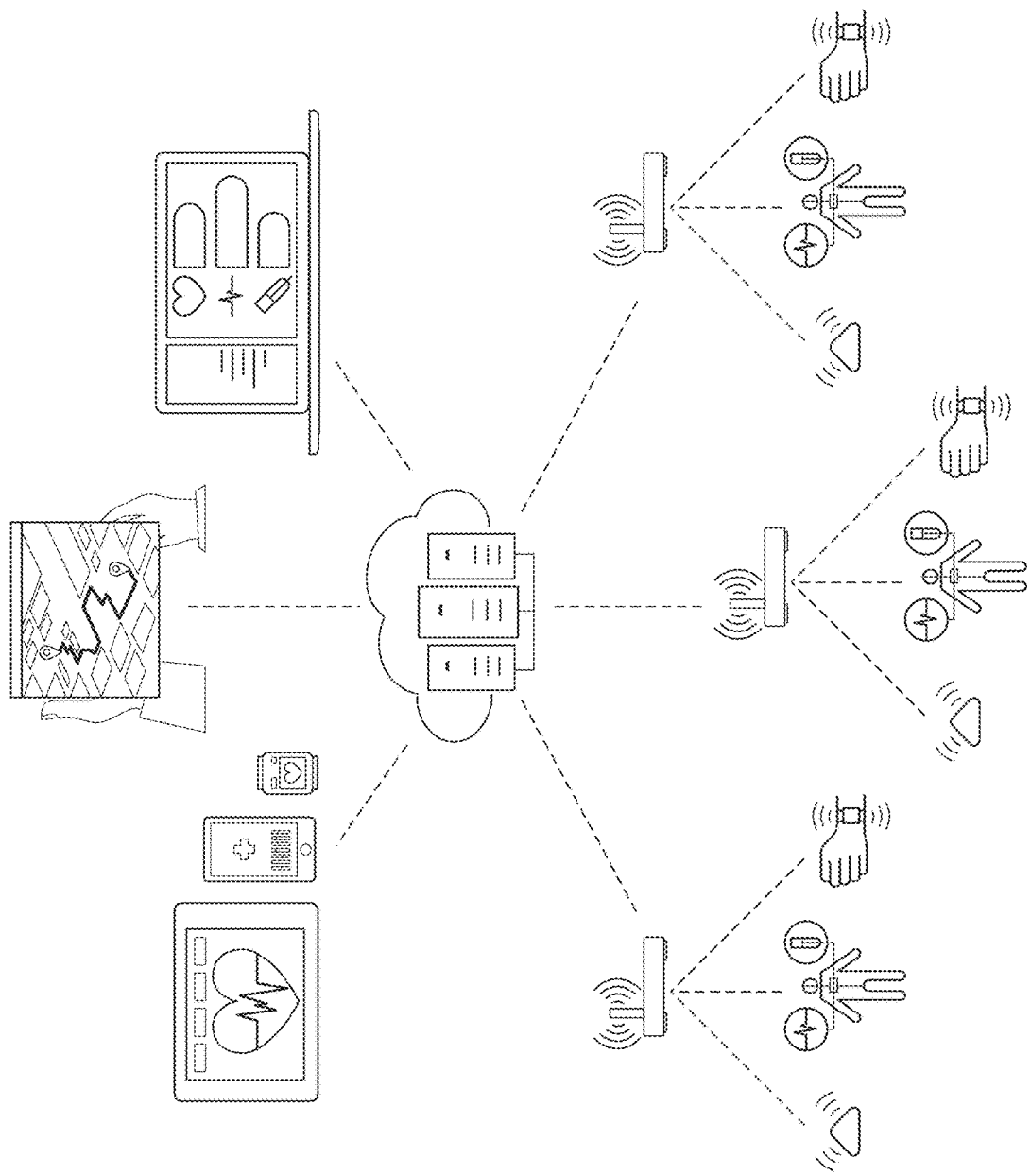
FIG. 7 is an embodiment of a system for determining a location and/or status of an asset.

As explained above, the system can also be used for the purpose of locating assets, or devices, anywhere in the specified area, such as a hospital/warehouse area, using an application that utilizes a computing device equipped with wireless capabilities, including but not limited to Bluetooth, Zigbee, NFC, Wi-Fi or any other wireless technologies. FIG. 7 illustrates an embodiment of a system for determining a location and/or status of an asset.

In some embodiments, in order to locate an asset, the asset is tagged with at least one small tag. The specified area is covered by network, such as a meshed network or any other network that allows for the determination of a general location of the asset in an area (e.g. the floor of a building, or north side). The signal between the asset and the network is strong enough such that the tag placed on the asset can receive commands or other information from the network.

For example, in a hospital implementations, a network of gateways can form an ubiquitous network including a hospital, such that any asset tagged with one of the BLE tags can be "seen" by the network and an approximate location determined by the network of gateways.

It can also be possible to aide in the location of assets that are hidden. For example, some of the smaller assets (for example, epidural pumps, electronic thermometers, etc.) can be "hidden" in drawers, closets, or other storage areas or containers. In some embodiment, the tags can be programmed to transmit every X seconds, avec 5<X<20 depending on the type of the assets. The X can be large in order to conserve battery power, but in return it makes it much longer to find the asset as the transmission rates are so low. Thus, X can be determined in order to balance power conservation and time to locate an asset. The mobile app can use RSSI levels.

Figure 8:
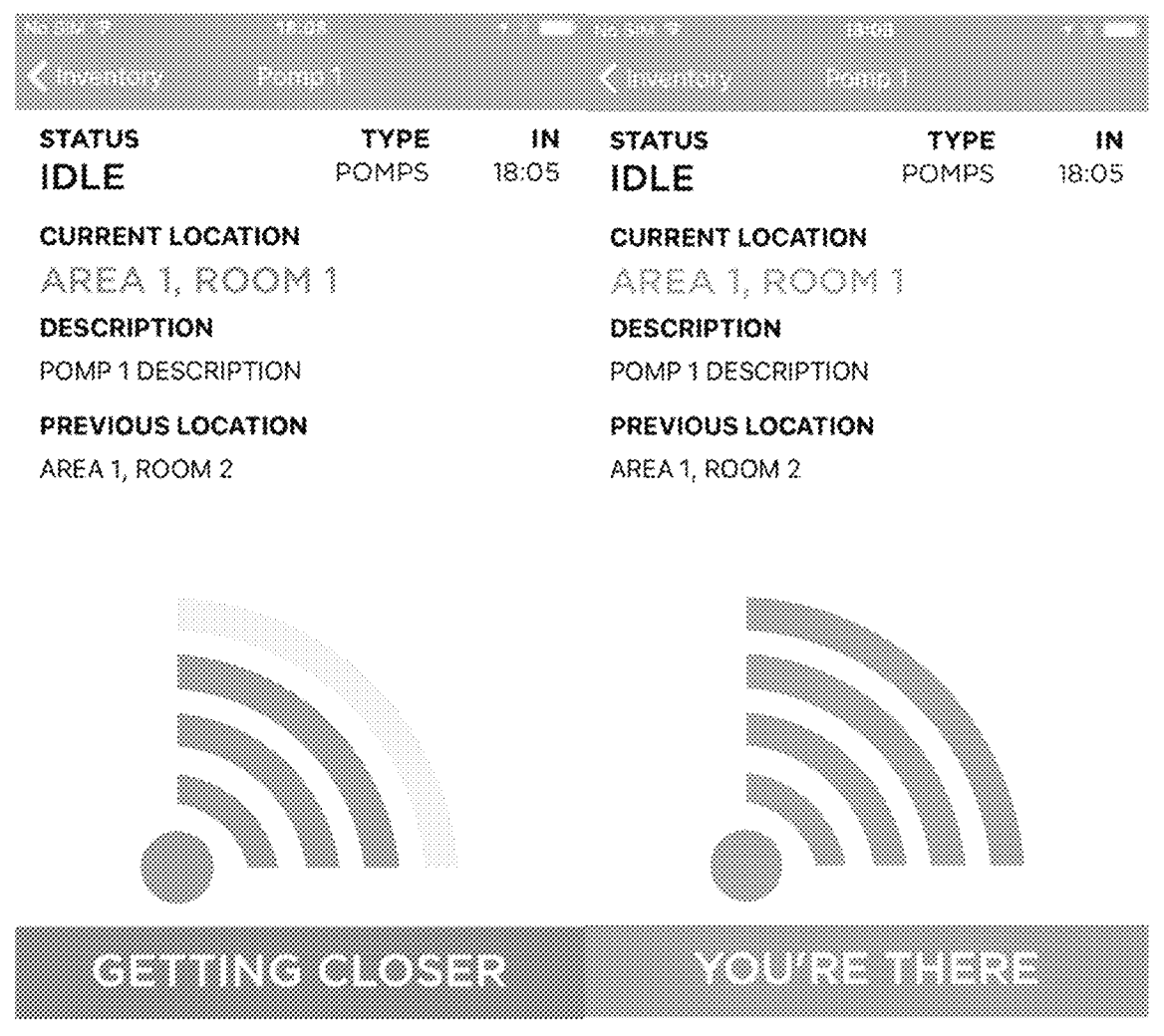
Figure 9:
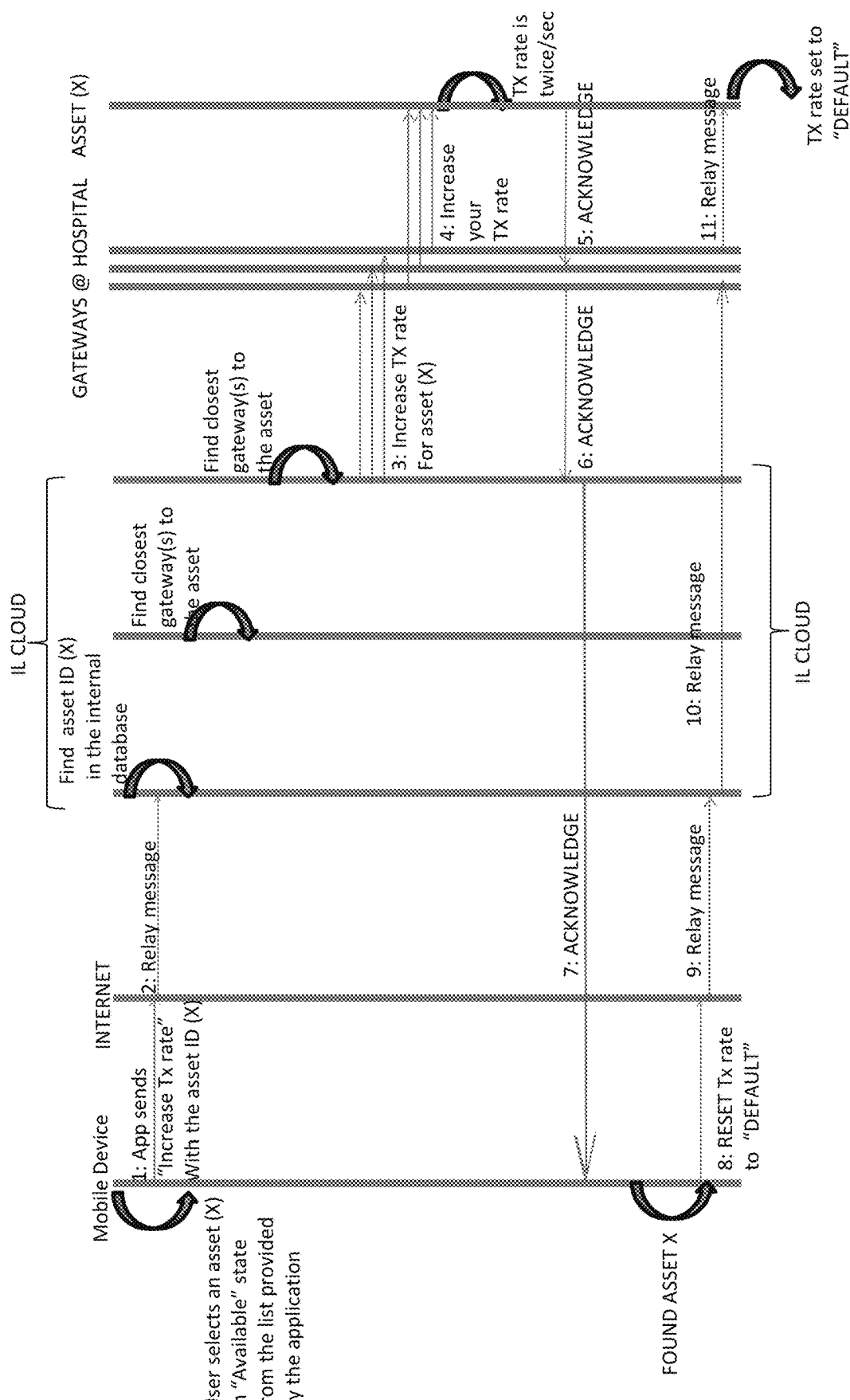
FIG. 9 illustrates an embodiment of a flowchart for determining the location of an asset using a change in a transmission rate of signals from the asset.

In some embodiments, a mobile application can be used which allows a user, such as a nurse or technician, to use their own device to locate an asset. FIG. 8 illustrates an embodiment of a user interface of a mobile application for locating an asset, and FIG. 9 illustrates an embodiment of a flowchart for determining the location of an asset using a change in a transmission rate of signals from the asset. The mobile application gives the list of assets with their status as described by the algorithms above. When a user selects a specific asset in the list in the mobile application for location, the mobile application (via the mobile device) sends a message to the central computer located in a network, such as the cloud, to increase the transmission rate of that specific BLE associated with the selected asset. For example, the application on Mobile device transmits a message to the central computer to increase the transmission rate to 0.5 times/second. The central computer decodes the message from the mobile application. For example, the central computer determines and finds the identity of the asset/device in its list of registered devices, and establishes which one or more gateways are the closest to the current location of the asset. The central computer sends a message to the tag on the asset to increase the transmission rate, for example, to 0.5 times/second. It will be understood that the transmission rate can be increase to any rate that is acceptable for locating the asset.

The one or more gateways receive the message and relay it the tag associated with the desired asset, for example using a radio physical layer radio and a proprietary protocol. Once the asset is located, the user selects the asset from the mobile application running on the mobile device which causes the transmission rate to return to its initial state. The transmission rate can be decreased to the initial rate, allowing the transmission rate from the asset to reset. In some embodiment, one or more safeguards can be put in place such as in the event that the RSSI received by the application on the mobile device is lower than Y dBm (Y depends on the power levels used by the tags to transmit and will be set as an offset to a nominal level and based on the line of sight attenuation of a radio wave at the operating frequency), which can reset the transmission rate to initial rates, and/or in the event that the accelerometer in the asset transitions from "not moving" to "moving" (the state transition can only be attributed in this case to the fact that it was moved by the nurse/technician).

The present disclosure is described with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of: a general purpose computer to alter its function to a special purpose; a special purpose computer; ASIC; or other programmable digital data processing apparatus, such that the instructions, which execute via the processor of the computer or other programmable data processing apparatus, implement the functions/acts specified in the block diagrams or operational block or blocks, thereby transforming their functionality in accordance with embodiments herein.

For the purposes of this disclosure a computer readable medium (or computer-readable storage medium/media)

stores computer data, which data can include computer program code (or computer-executable instructions) that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

For the purposes of this disclosure the term "server" or central computer should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For the purposes of this disclosure a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a wired or wireless line or link, for example.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly.

A wireless network may further employ a plurality of network access technologies, including Wi-Fi, Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For purposes of this disclosure, a client device, such as, for example, an asset or an aggregator, may include a computing device capable of sending or receiving signals, such as via a wired or a wireless network. A client device may, for example, include a desktop computer or a portable device, such as a cellular telephone, a smart phone, a display pager, a radio frequency (RF) device, an infrared (IR) device, a Near Field Communication (NFC) device, a Personal Digital Assistant (PDA), a handheld computer, a tablet computer, a phablet, a laptop computer, a set top box, a wearable computer, smart watch, an integrated or distributed device combining various features, such as features of the forgoing devices, or the like.

A client device may vary in terms of capabilities or features. Claimed subject matter is intended to cover a wide range of potential variations. For example, a simple smart phone, phablet or tablet may include a numeric keypad or a display of limited functionality, such as a monochrome liquid crystal display (LCD) for displaying text. In contrast, however, as another example, a web-enabled client device may include a high-resolution screen, one or more physical or virtual keyboards, mass storage, one or more accelerometers, one or more gyroscopes, global positioning system (GPS) or other location-identifying type capability, or a display with a high degree of functionality, such as a touch-sensitive color 2D or 3D display, for example.

A client device may include or may execute a variety of operating systems, including a personal computer operating system, such as a Windows, iOS or Linux, or a mobile operating system, such as iOS, Android, or Windows Mobile, or the like.

A client device may include or may execute a variety of possible applications, such as a client software application enabling communication with other devices, such as communicating one or more messages, such as via email, for example Yahoo!® Mail, short message service (SMS), or multimedia message service (MMS), for example Yahoo! Messenger®, including via a network, such as a social network, including, for example, Tumblr®, Facebook®, LinkedIn®, Twitter®, Flickr®, or Google+®, Instagram™, to provide only a few possible examples. A client device may also include or execute an application to communicate content, such as, for example, textual content, multimedia content, or the like. A client device may also include or execute an application to perform a variety of possible tasks, such as browsing, searching, playing or displaying various forms of content, including locally stored or streamed video, or games. The foregoing is provided to illustrate that claimed subject matter is intended to include a wide range of possible features or capabilities.

Figure 10:
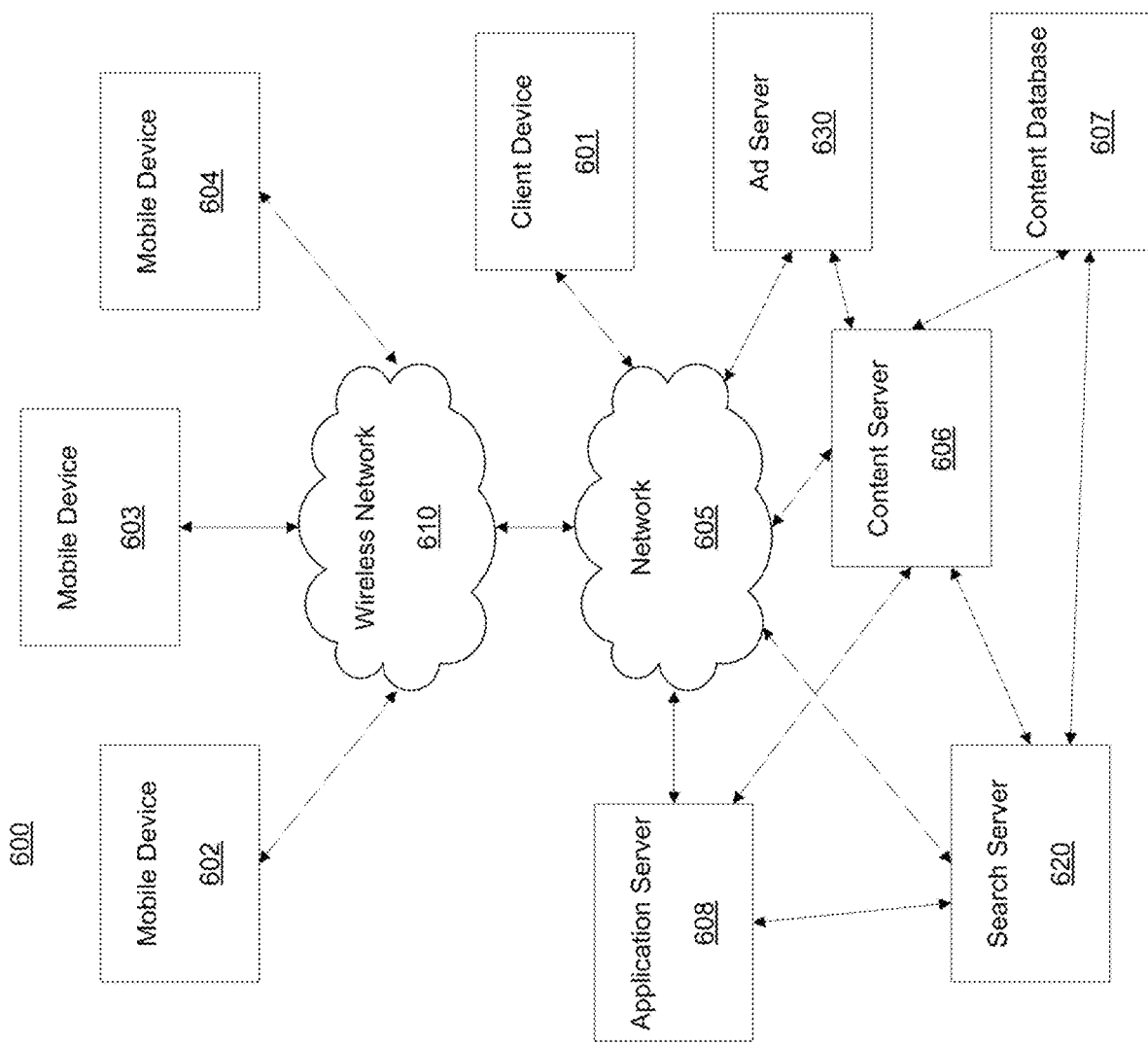
FIG. 10 illustrates an embodiment of a system that is configured to determine a location and/or status of an asset.

FIG. 10 illustrates an embodiment of a system 600 that is configured to determine a location and/or status of an asset. Not all the components may be required to practice the disclosure, and variations in the arrangement and type of the components may be made without departing from the spirit or scope of the disclosure. As shown, system 600 of FIG. 10 includes a network 605, such as local area networks ("LANs")/wide area networks ("WANs"), a wireless network 610, mobile devices (client devices) 602-604, and a client device 601. One or more of mobile devices 602-604 and/or client device 601 may be an asset and/or an aggregator. FIG. 10 additionally includes a variety of servers (e.g., central computer), such as a content server 606, an application (or "App") server 608, a search server 620, and an advertising ("ad") server 630.

The mobile devices 602-604 can have a variety of forms. In some embodiments, the mobile devices 602-604 can include virtually any portable computing device capable of receiving and sending a message over a network, such as the network 605, the wireless network 610, or the like. The mobile devices 602-604 may also be described generally as client devices that are configured to be portable. Thus, the mobile devices 602-604 may include virtually any portable computing device capable of connecting to another computing device and receiving information. Such devices include, but are not limited to, multi-touch and portable devices such as, cellular telephones, smart phones, display pagers, radio frequency (RF) devices, infrared (IR) devices, Personal Digital Assistants (PDAs), handheld computers, laptop computers, wearable computers, smart watch, tablet computers, phablets, integrated devices combining one or more of the preceding devices, and the like. As such, mobile devices 602-604 can range widely in terms of capabilities and features. For example, a cell phone may have a numeric keypad and a few lines of monochrome LCD display on which only text may be displayed. In another example, a web-enabled mobile device may have a touch sensitive screen, a stylus, and an HD display in which both text and graphics may be displayed.

A web-enabled mobile device can include a browser application that is configured to receive and to send web pages, web-based messages, and the like. The browser application may be configured to receive and display graphics, text, multimedia, and the like, employing virtually any web based language, including a wireless application protocol messages (WAP), and the like. In some embodiments, the browser application is enabled to employ Handheld Device Markup Language (HDML), Wireless Markup Language (WML), WMLScript, JavaScript, Standard Generalized Markup Language (SMGL), HyperText Markup Language (HTML), eXtensible Markup Language (XML), and the like, to display and send a message.

The mobile devices 602-604 also can include at least one client application that is configured to receive content from another computing device. The client application can include a capability to provide and receive textual content, graphical content, audio content, and the like. The client application may further provide information that identifies itself, including a type, capability, name, and the like. In some embodiments, the mobile devices 602-604 can uniquely identify themselves through any of a variety of mechanisms, including a phone number, Mobile Identification Number (MIN), an electronic serial number (ESN), or other mobile device identifier.

In some embodiments, the mobile devices 602-604 may also communicate with non-mobile client devices, such as the client device 601, or the like. In some embodiments, such communications can include sending and/or receiving messages, searching for, viewing and/or sharing photographs, audio clips, video clips, or any of a variety of other forms of communications. The client device 601 can include virtually any computing device capable of communicating over a network to send and receive information. The set of such devices may include devices that typically connect using a wired or wireless communications medium such as personal computers, multiprocessor systems, microprocessor-based or programmable consumer electronics, network PCs, or the like. Thus, the client device 601 can also have differing capabilities for displaying navigable views of information.

The client device 601 and/or mobile devices 602-604 can be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like.

The wireless network 610 can be configured to couple the mobile devices 602-604 and its components with the network 605. The wireless network 610 may include any of a variety of wireless sub-networks that may further overlay stand-alone ad-hoc networks, and the like, to provide an infrastructure-oriented connection for the mobile devices 602-604. Such sub-networks may include mesh networks, Wireless LAN (WLAN) networks, cellular networks, and the like.

The network 605 can be configured to couple content server 606, application server 608, or the like, with other computing devices, including but not limited to the client device 601, and through wireless network 610 to the mobile devices 602-604. The network 605 is enabled to employ any form of computer readable media for communicating information from one electronic device to another. Also, the network 605 can include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another, and/or other computing devices.

The various networks can employ various protocols to allow for communication over the network. Signal packets communicated via a network, such as a network of participating digital communication networks, may be compatible with or compliant with one or more protocols. Signaling formats or protocols employed may include, for example, TCP/IP, UDP, QUIC (Quick UDP Internet Connection), DECnet, NetBEUI, IPX, APPLETALK™, or the like. Versions of the Internet Protocol (IP) may include IPv4 or IPv6. The Internet refers to a decentralized global network of networks. The Internet includes local area networks (LANs), wide area networks (WANs), wireless networks, or long haul public networks that, for example, allow signal packets to be communicated between LANs. Signal packets may be communicated between nodes of a network, such as, for example, to one or more sites employing a local network address. A signal packet may, for example, be communicated over the Internet from a user site via an access node coupled to the Internet. Likewise, a signal packet may be forwarded via network nodes to a target site coupled to the network via a network access node, for example. A signal packet communicated via the Internet may, for example, be routed via a path of gateways, servers, etc. that may route the signal packet in accordance with a target address and availability of a network path to the target address.

In some embodiments, the system herein can also be utilized within or accessible to an electronic social networking site. A social network refers generally to an electronic network of individuals, such as acquaintances, friends, family, colleagues, or co-workers, that are coupled via a communications network or via a variety of sub-networks. Potentially, additional relationships may subsequently be formed as a result of social interaction via the communications network or sub-networks. In some embodiments, multi-modal communications may occur between members of the social network. Individuals within one or more social networks may interact or communication with other members of a social network via a variety of devices. Multi-modal communication technologies refers to a set of technologies that permit interoperable communication across multiple devices or platforms, such as cell phones, smart phones, tablet computing devices, phablets, personal computers, televisions, set-top boxes, SMS/MMS, email, instant messenger clients, forums, social networking sites, or the like.

In some embodiments, the network 610 and/or the network 605 can comprise a content distribution network(s). A "content delivery network" or "content distribution network" (CDN) generally refers to a distributed content delivery system that comprises a collection of computers or computing devices linked by a network or networks. A CDN may employ software, systems, protocols or techniques to facilitate various services, such as storage, caching, communication of content, or streaming media or applications. A CDN may also enable an entity to operate or manage another's site infrastructure, in whole or in part.

In some embodiment, the content server 606 can include a device that includes a configuration to provide content via a network to another device. The content server 606 can, for example, host a site or service, such as streaming media site/service (e.g., Netflix®), an email platform or social networking site, or a personal user site (such as a blog, vlog, online dating site, and the like). The content server 606 may also host a variety of other sites, including, but not limited to business sites, educational sites, dictionary sites, encyclopedia sites, wikis, financial sites, government sites, and the like. Various devices can operate as the content server 606, including but not limited to personal computers desktop computers, multiprocessor systems, microprocessor-based or programmable consumer electronics, network PCs, servers, and the like.

The content server 606 can further provide a variety of services that include, but are not limited to, streaming and/or downloading media services, search services, email services, photo services, web services, social networking services, news services, third-party services, audio services, video services, instant messaging (IM) services, SMS services, MMS services, FTP services, voice over IP (VOIP) services, or the like. Such services, for example a video application and/or video platform, can be provided via the application server 608, whereby a user is able to utilize such service upon the user being authenticated, verified or identified by the service. Examples of content may include images, text, audio, video, or the like, which may be processed in the form of physical signals, such as electrical signals, for example, or may be stored in memory, as physical states, for example.

An ad server 630 comprises a server that stores online advertisements for presentation to users. "Ad serving" refers to methods used to place online advertisements on websites, in applications, or other places where users are more likely to see them, such as during an online session or during computing platform use, for example. Various monetization techniques or models may be used in connection with sponsored advertising, including advertising associated with user. Such sponsored advertising includes monetization techniques including sponsored search advertising, non-sponsored search advertising, guaranteed and non-guaranteed delivery advertising, ad networks/exchanges, ad targeting, ad serving and ad analytics. Such systems can incorporate near instantaneous auctions of ad placement opportunities during web page creation, (in some cases in less than 500 milliseconds) with higher quality ad placement opportunities resulting in higher revenues per ad. That is, advertisers will pay higher advertising rates when they believe their ads are being placed in or along with highly relevant content that is being presented to users. Reductions in the time needed to quantify a high quality ad placement offers ad platforms competitive advantages. Thus higher speeds and more relevant context detection improve these technological fields.

For example, a process of buying or selling online advertisements may involve a number of different entities, including advertisers, publishers, agencies, networks, or developers. To simplify this process, organization systems called "ad exchanges" may associate advertisers or publishers, such as via a platform to facilitate buying or selling of online advertisement inventory from multiple ad networks. "Ad networks" refers to aggregation of ad space supply from publishers, such as for provision en masse to advertisers. For web portals like Yahoo!®, advertisements may be displayed on web pages or in apps resulting from a user-defined search based at least in part upon one or more search terms. Advertising may be beneficial to users, advertisers or web portals if displayed advertisements are relevant to interests of one or more users. Thus, a variety of techniques have been developed to infer user interest, user intent or to subsequently target relevant advertising to users. One approach to presenting targeted advertisements includes employing demographic characteristics (e.g., age, income, sex, occupation, etc.) for predicting user behavior, such as by group. Advertisements may be presented to users in a targeted audience based at least in part upon predicted user behavior(s).

Another approach includes profile-type ad targeting. In this approach, user profiles specific to a user may be generated to model user behavior, for example, by tracking a user's path through a web site or network of sites, and compiling a profile based at least in part on pages or advertisements ultimately delivered. A correlation may be identified, such as for user purchases, for example. An identified correlation may be used to target potential purchasers by targeting content or advertisements to particular users. During presentation of advertisements, a presentation system may collect descriptive content about types of advertisements presented to users.

A broad range of descriptive content may be gathered, including content specific to an advertising presentation system. Advertising analytics gathered may be transmitted to locations remote to an advertising presentation system for storage or for further evaluation. Where advertising analytics transmittal is not immediately available, gathered advertising analytics may be stored by an advertising presentation system until transmittal of those advertising analytics becomes available.

The servers 606, 608, 620, and 630 can be capable of sending or receiving signals, such as via a wired or wireless network, or may be capable of processing or storing signals, such as in memory as physical memory states. Devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally, a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

In some embodiments, users are able to access services provided by the servers 606, 608, 620, and/or 630. This can include in a non-limiting example, authentication servers, search servers, email servers, social networking services servers, SMS servers, IM servers, MMS servers, exchange servers, photo-sharing services servers, and travel services servers, via the network 605 using their various devices 601-604. In some embodiments, applications, such as a streaming video application (e.g., Netflix®, Hulu®, iTunes®, Amazon Prime®, HBO Go®, and the like), blog, photo storage/sharing application or social networking application (e.g., Flickr®, Tumblr®, and the like), can be hosted by the application server 608 (or the content server 606, the search server 620, and the like). Thus, the application server 608 can store various types of applications and application related information including application data and user profile information (e.g., identifying and behavioral information associated with a user). It should also be understood that the content server 606 can also store various types of data related to the content and services provided by the content server 606 in an associated content database 607.

Moreover, although FIG. 10 illustrates the servers 606, 608, 620, and 630 as single computing devices, respectively, in some embodiments, one or more functions of the servers 606, 608, 620, and/or 630 can be distributed across one or more distinct computing devices. Moreover, in some embodiments, the servers 606, 608, 620 and/or 630 may be integrated into a single computing device.

Figure 11:
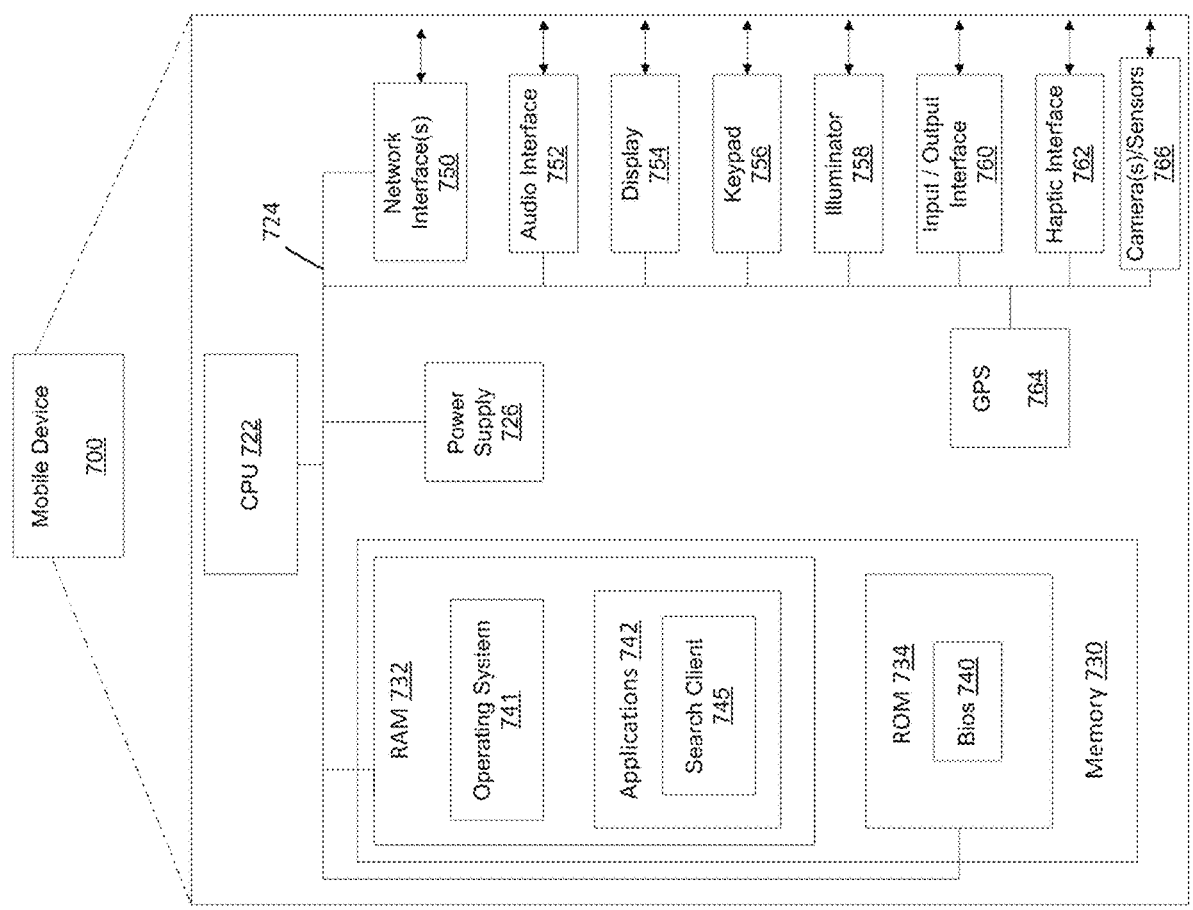
FIG. 11 illustrates an exemplary embodiment of a client device.

FIG. 11 illustrates an exemplary embodiment of a client device (e.g., an asset). A client device 700 can include many more or less components than those shown in FIG. 11. The client device 700 can represent, for example, client devices discussed above in relation to FIG. 10.

As shown in FIG. 11, the client device 700 includes a processing unit (CPU) 722 in communication with a mass memory 730 via a bus 724. The client device 700 also includes a power supply 726, one or more network interfaces 750, an audio interface 752, a display 754, a keypad 756, an illuminator 758, an input/output interface 760, a haptic interface 762, an optional global positioning systems (GPS) receiver 764 and a camera(s) or other optical, thermal or electromagnetic sensors 766. The client device 700 can include one camera/sensor 766, or a plurality of cameras/sensors 766, as understood by those of skill in the art. The positioning of the camera(s)/sensor(s) 766 on the client device 700 can change per client device 700 model, per client device 700 capabilities, and the like, or some combination thereof.

The power supply 726 provides power to the client device 700. A rechargeable or non-rechargeable battery may be used to provide power. The power may also be provided by an external power source, such as an AC adapter or a powered docking cradle that supplements and/or recharges a battery.

The client device 700 may optionally communicate with a base station (not shown), or directly with another computing device. The network interface 750 includes circuitry for coupling the client device 700 to one or more networks, and is constructed for use with one or more communication protocols and technologies as discussed above. The network interface 750 is sometimes known as a transceiver, transceiving device, or network interface card (NIC).

The audio interface 752 can be arranged to produce and receive audio signals such as the sound of a human voice. For example, the audio interface 752 can be coupled to a speaker and microphone (not shown) to enable telecommunication with others and/or generate an audio acknowledgement for some action. The display 754 can be a liquid crystal display (LCD), gas plasma, light emitting diode (LED), or any other type of display used with a computing device. The display 754 can also include a touch sensitive screen arranged to receive input from an object such as a stylus or a digit from a human hand.

The keypad 756 can comprise any input device arranged to receive input from a user. For example, the keypad 756 can include a push button numeric dial, or a keyboard. The keypad 756 can also include command buttons that are associated with selecting and sending images. Illuminator 758 may provide a status indication and/or provide light. Illuminator 758 may remain active for specific periods of time or in response to events. For example, when the illuminator 758 is active, it can backlight the buttons on the keypad 756 and stay on while the client device is powered. Also, the illuminator 758 can backlight these buttons in various patterns when particular actions are performed, such as dialing another client device. Illuminator 758 may also cause light sources positioned within a transparent or translucent case of the client device to illuminate in response to actions.

The client device 700 also comprises input/output interface 760 for communicating with external devices, such as a headset, or other input or output devices not shown in FIG. 11. The input/output interface 760 can utilize one or more communication technologies, such as USB, infrared, Bluetooth™, or the like. Haptic interface 762 is arranged to provide tactile feedback to a user of the client device. For example, the haptic interface 762 can be employed to vibrate the client device 700 in a particular way when the client device 700 receives a communication from another user.

Optional GPS transceiver 764 can determine the physical coordinates of The client device 700 on the surface of the Earth, which typically outputs a location as latitude and longitude values. GPS transceiver 764 can also employ other geo-positioning mechanisms, including, but not limited to, triangulation, assisted GPS (AGPS), E-OTD, CI, SAI, ETA, BSS or the like, to further determine the physical location of Client device 700 on the surface of the Earth. It is understood that under different conditions, GPS transceiver 764 can determine a physical location within millimeters for the client device 700; and in other cases, the determined physical location may be less precise, such as within a meter or significantly greater distances. In some embodiments, however, the client device can through other components, provide other information that may be employed to determine a physical location of the device, including for example, a MAC address, Internet Protocol (IP) address, or the like.

Mass memory 730 includes a RAM 732, a ROM 734, and other storage means. The mass memory 730 illustrates another example of computer storage media for storage of information such as computer readable instructions, data structures, program modules or other data. The mass memory 730 stores a basic input/output system ("BIOS") 740 for controlling low-level operation of the client device 700. The mass memory 730 also stores an operating system 741 for controlling the operation of the client device 700. It will be appreciated that this component may include a general purpose operating system such as a version of UNIX, or LINUX™, or a specialized client communication operating system such as Windows Client™, or the Symbian® operating system. The operating system 741 can include, or interface with a Java virtual machine module that enables control of hardware components and/or operating system operations via Java application programs.

The memory 730 can further include one or more data stores, which can be utilized by the client device 700 to store, among other things, applications 742 and/or other data. For example, data stores may be employed to store information that describes various capabilities of the client device 700. The information may then be provided to another device based on any of a variety of events, including being sent as part of a header during a communication, sent upon request, or the like. At least a portion of the capability information may also be stored on a disk drive or other storage medium (not shown) within the client device 700.

The applications 742 can include computer executable instructions which, when executed by the client device 700, transmit, receive, and/or otherwise process audio, video, images, and enable telecommunication with a server and/or another user of another client device. Other examples of application programs or "apps" in some embodiments include browsers, calendars, contact managers, task managers, transcoders, photo management, database programs, word processing programs, security applications, spreadsheet programs, games, search programs, and so forth. The applications 742 can also include a search client 745 that is configured to send, to receive, and/or to otherwise process a search query and/or search result using any known or to be known communication protocols. Although a single search client 745 is illustrated it should be clear that multiple search clients may be employed. For example, one search client may be configured to enter a search query message, where another search client manages search results, and yet another search client is configured to manage serving advertisements, IMs, emails, and other types of known messages, or the like.

Figure 12:
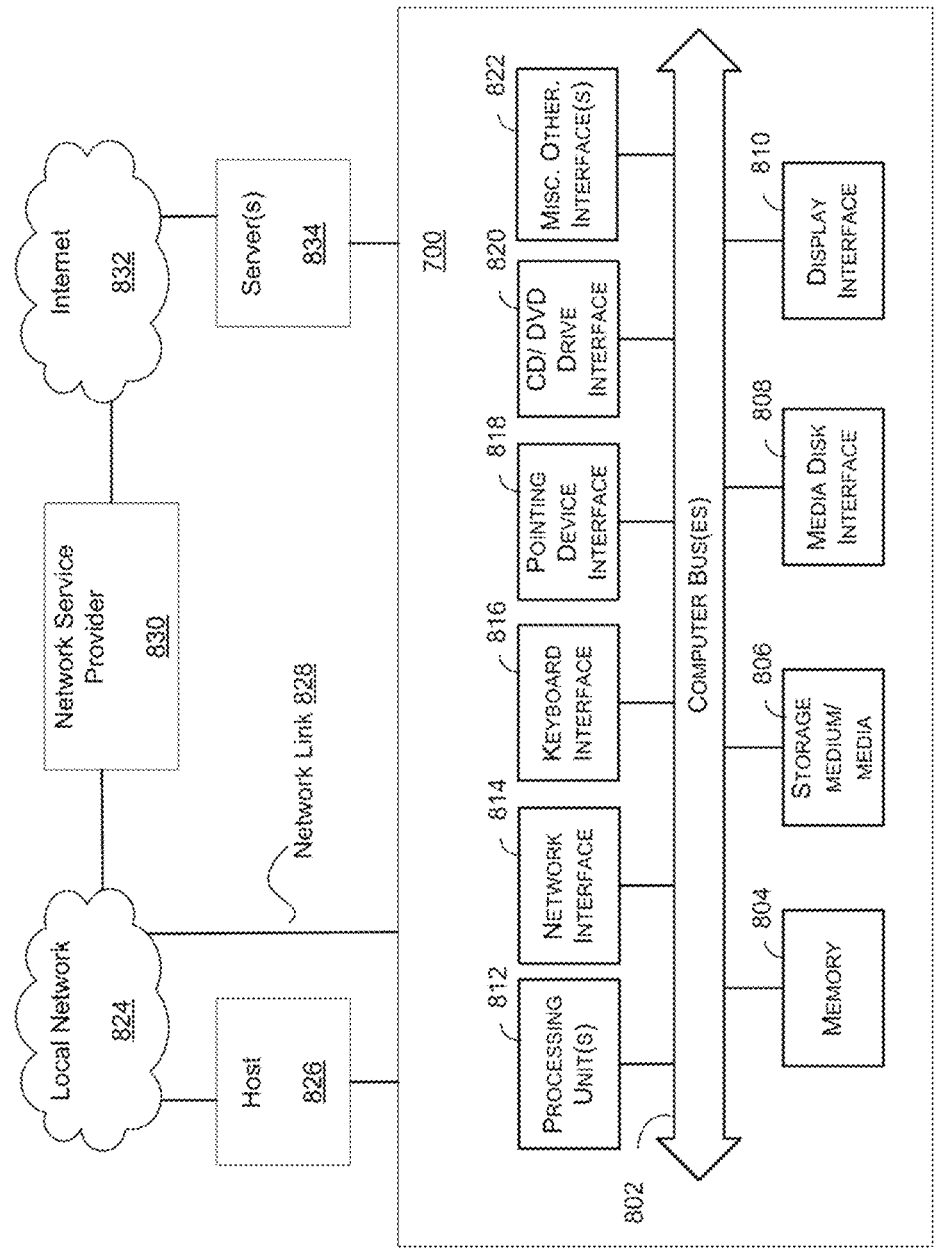
FIG. 12 illustrates an embodiment an internal architecture of a computing device, computing system, and computing platform.

As shown in FIG. 12, in some embodiments an internal architecture 800 of a computing device(s) (e.g., an asset), computing system, computing platform and the like can include one or more processing units, processors, or processing cores, (also referred to herein as CPUs) 812, which interface with at least one computer bus 802. Also interfacing with the computer bus 802 are, for example, a computer-readable medium, or media, 806, a network interface 814, a memory 804, e.g., random access memory (RAM), run-time transient memory, read only memory (ROM), a media disk drive interface 820 as an interface for a drive that can read and/or write to media including removable media such as floppy, CD-ROM, DVD, media, a display interface 710 as interface for a monitor or other display device, a keyboard interface 816 as interface for a keyboard, a pointing device interface 818 as an interface for a mouse or other pointing device, and miscellaneous other interfaces not shown individually, such as parallel and serial port interfaces and a universal serial bus (USB) interface.

The memory 804 interfaces with the computer bus 802 so as to provide information stored in memory 804 to CPU 812 during execution of software programs such as an operating system, application programs, device drivers, and software modules that comprise program code, and/or computer executable process steps, incorporating functionality described herein, e.g., one or more of process flows described herein. CPU 812 first loads computer executable process steps from storage, e.g., the memory 804, computer readable storage medium/media 806, removable media drive, and/or other storage device. CPU 812 can then execute the stored process steps in order to execute the loaded computer-executable process steps. Stored data, e.g., data stored by a storage device, can be accessed by CPU 812 during the execution of computer-executable process steps.

Persistent storage, e.g., medium/media 806, can be used to store an operating system and one or more application programs. Persistent storage can also be used to store device drivers, such as one or more of a digital camera driver, monitor driver, printer driver, scanner driver, or other device drivers, web pages, content files, playlists and other files. Persistent storage can further include program modules and data files used to implement one or more embodiments of the present disclosure.

The network link 828 can provide information communication using transmission media through one or more networks to other devices that use or process the information. For example, the network link 828 can provide a connection through the local network 824 to a host computer 826 or to equipment operated by a Network or Internet Service Provider (ISP) 830. ISP equipment in turn provides data communication services through the public, worldwide packet-switching communication network of networks now commonly referred to as the Internet 832.

A computer called a server host 834 connected to the Internet 832 hosts a process that provides a service in response to information received over the Internet 832. For example, the server host 834 hosts a process that provides information representing video data for presentation at the display 810. Various components of the system 800 can be deployed in various configurations within other computer systems, e.g., host and server.

In some embodiments, the computer system 800 can be used for implementing some or all of the techniques described herein. In some embodiments, those techniques are performed by computer system 800 in response to the processing unit 812 executing one or more sequences of one or more processor instructions contained in the memory 804. Such instructions, also called computer instructions, software and program code, can be read into the memory 804 from another computer-readable medium 806 such as storage device or network link. Execution of the sequences of instructions contained in the memory 804 causes the processing unit 812 to perform one or more of the method steps described herein. In some embodiments, hardware, such as ASIC, can be used in place of or in combination with software. Thus, embodiments of the present disclosure are not limited to any specific combination of hardware and software, unless otherwise explicitly stated herein.

The signals transmitted over network link and other networks through communications interface, carry information to and from the computer system 800. The computer system 800 can send and receive information, including program code, through the networks, among others, through network link and communications interface. In an example using the Internet, a server host transmits program code for a particular application, requested by a message sent from computer, through Internet, ISP equipment, local network and communications interface. The received code may be executed by the processor 802 as it is received, or may be stored in the memory 804 or in storage device or other non-volatile storage for later execution, or both.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium for execution by a processor. Modules may be integral to one or more servers, or be loaded and executed by one or more servers. One or more modules may be grouped into an engine or an application.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

What is claimed is:

1. A method comprising:
   transmitting a plurality of parameters relating to a medical asset to a central computer, the medical asset including one or more tags positioned thereon for transmitting the plurality of parameters; and
   determining a status of the medical asset based on the plurality of parameters using an algorithm on the central computer, the plurality of parameters being weighted for use by the algorithm;
   wherein at least one of the plurality of parameters is configured to be an overriding parameter which automatically defines the status of the medical asset and overrides the status of the medical asset,
   wherein the status of the medical asset is used to compile a profile of the medical asset to determine a usage rate of the medical asset, the profile of the asset over time is formed from a plurality of statuses over time, and wherein increasing the amount of statuses in the time period is effective to increase the accuracy of the profile of the asset.

2. The method of claim 1, wherein the plurality of parameters comprises accelerometer data relating to movement of the medical asset through a specified area such that the movement of the medical asset is used to determine the status of the medical asset.

3. The method of claim 1, wherein the plurality of parameters comprises temperature data relating to a temperature of the medical asset relative to ambient temperature.

4. The method of claim 1, wherein the plurality of parameters comprises location data relating to the location of the medical asset.

5. The method of claim 4, wherein a geo-fence defining an area using a plurality of aggregators is used to determine the location data.

6. The method of claim 5, wherein each aggregator in the plurality of aggregators communicates with neighboring aggregators and with the central computer to determine the location data within the area of the geo-fence.

7. The method of claim 1, wherein the status of the medical asset is used to compile a profile of the medical asset over time to determine a usage rate of the medical asset.

8. A method comprising:
transmitting parameter data relating to a medical asset to a central computer, the asset including one or more tags positioned thereon for transmitting the parameter data; and
determining a status of the medical asset based on the parameter data using an algorithm on the central computer;
wherein the status of the medical asset is used to compile a profile of the medical asset over time to determine a usage rate of the medical asset,
wherein the profile of the asset over time is formed from a plurality of statuses over time, and wherein increasing the amount of statuses in the time period is effective to increase the accuracy of the profile of the asset.

9. The method of claim 8, wherein the profile over time is determined using accelerometer data relating to movement of the asset such that the movement of the asset is used to determine the status of the asset over a specified time period.

10. The method of claim 8, wherein the profile of the medical asset over time correlated to the usage of the asset over time.

11. The method of claim 8, wherein the one or more tags receive parameter data from a plurality of sensors.

12. The method of claim 8, wherein the medical asset is in the form a medication dispenser, and the profile determines if a medication stored in the medication dispenser is being taken by a patient at a prescribed dosage rate.

13. The method of claim 12, wherein movement of the medication dispenser can be detected, including movement associated with opening the medication dispenser.

14. The method of claim 8, wherein the parameter data comprises accelerometer data relating to movement of the medical asset through a specified area such that the movement of the medical asset is used to determine the status of the medical asset.

15. The method of claim 8, wherein the parameter data comprises temperature data relating to a temperature of the medical asset relative to ambient temperature.

16. The method of claim 8, wherein the parameter data comprises location data relating to the location of the medical asset.

17. The method of claim 16, wherein a geo-fence defining an area using a plurality of aggregators is used to determine the location data.

* * * * *